(12) United States Patent
Lam et al.

(10) Patent No.: US 6,274,596 B1
(45) Date of Patent: Aug. 14, 2001

(54) BENZOQUINOLINE DERIVATIVES USEFUL AS ANTIBACTERIAL AGENTS

(75) Inventors: Kelvin Lam, Belmont; Vincent Boyd, Pepperell; Yi Bin Xiang, Acton, all of MA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/413,405

(22) Filed: Oct. 6, 1999

Related U.S. Application Data

(60) Provisional application No. 60/103,822, filed on Oct. 9, 1998.

(51) Int. Cl.$^7$ .......................... A61K 31/47; A61K 31/445
(52) U.S. Cl. ........................ 514/314; 514/317; 514/324
(58) Field of Search .................................. 514/314, 317, 514/324

(56) References Cited

U.S. PATENT DOCUMENTS 4,224,448   9/1980   Haber et al. ................. 546/167

FOREIGN PATENT DOCUMENTS 2 604 705   4/1988   (FR) .

OTHER PUBLICATIONS

Chen, Chang et al., "Studies on New Antimalarials—Synthesis of Heterocyclic Compounds Carrying Double Mannich Basic Chains of p–Aminophenol", Yaoxue Xuebao (1982), 17(2), 12–17, 1982 XP000910813, abstract; table 5.

(List continued on next page.)

Primary Examiner—Kevin E. Weddington
(74) Attorney, Agent, or Firm—Darby & Darby

(57) ABSTRACT

Disclosed are pharmaceutical compositions and formulations comprising benzoquinoline derivatives having the formula (I) to (V), wherein formula (I) is:

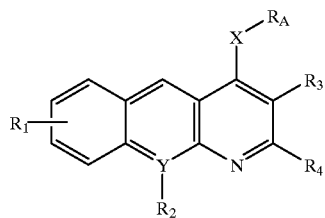

X is selected from the group consisting of O, S, $CH_2$, $CH_2$–$CH_2$, C=O or $NR_B$;
Y is C or N;
$R_1$, $R_2$, $R_3$ and $R_4$ are independently selected from the group consisting of hydrogen, halogen, linear or branched chain lower alky, alkenyl, alkynyl, alkoxy or acyl;

X-$R_A$ and $R_3$, or $R_3$ and $R_4$, are optionally linked together to form a $C_3$–$C_4$ alkylene bridge, where X is $CH_2$ or C=O; provided that:

when X is $NR_B$, then
  (a) $R_B$ is hydrogen, and $R_A$ is a linear or branched chain lower alkyl, aryl, heteroaryl, cycloalkyl or cycloalkenyl optionally interrupted by at least one heteroatom, said alkyl, alkenyl, alkynyl, aryl, heteroaryl, cycloalkyl or cycloalkenyl being optionally substituted singly or plurally by at least one of a linear or branched chain lower alkyl, alkenyl, alkynyl, acyl, alkoxy, or cycloalkyl optionally interrupted by at least one heteroatom and optionally substituted by at least one linear or branched chain lower alkyl, alkenyl, alkynyl, acyl, or alkoxy, or a linear or branched chain lower alkyl mono- or dialkylamino, (linear or branched chain lower alkyl N-mono- or N,N-dialkylamino)(lower alkyl), (linear or branched chain lower alkyl N-mono- or N,N-dialkyl)carbamyl, aryl or heteroaryl; or
  (b) X, $R_A$ and $R_B$ together form a ring system comprising from about five to about twelve linked carbon atoms, said system being optionally interrupted by at least one heteroatom, optionally mono- or polyunsaturated and optionally substituted singly or plurally by at least one of a linear or branched chain lower alkyl, alkenyl, alkynyl, acyl, or alkoxy, a linear or branched chain lower alkyl N-mono- or N,N-dialkylamino, (linear or branched chain lower alkyl N-mono- or N,N-dialkylarnino)(lower alkyl), halogen, cyano, trifluoromethyl, nitro, aryl or heteroaryl; and when X is O, S, $CH_2$, $CH_2$–$CH_2$ or C=O, then
  (a) $R_A$ is hydrogen or a linear or branched chain lower alkyl, alkenyl, alkynyl, aryl or heteroaryl, said alkyl, alkenyl, alkynyl, aryl or heteroaryl being optionally substituted singly or plurally by at least one of a linear or branched chain lower alkyl, alkenyl, alkynyl, acyl, or alkoxy, a linear or branched chain lower alkyl N-mono- or N,N-dialkylamino, (linear or branched chain lower alkyl N-mono- or N,N-dialkylamino)(lower alkyl), halogen, cyano, trifluoromethyl, nitro, aryl or heteroaryl; and
  (b) $R_3$ is a linear or branched chain lower alkyl substituted by hydroxyphenyl or linear or branched chain lower alkoxyphenyl singly or plurally substituted by $CH_2NR_CR_D$ wherein N, $R_C$ and $R_D$ together form a ring system comprising from about five to about twelve linked carbon atoms, said system being optionally interrupted by at least one heteroatom, optionally mono- or polyunsaturated and optionally substituted singly or plurally by at least one of a linear or branched chain lower alkyl, acyl, or alkoxy, a linear or branched chain lower alkyl N-mono- or N,N-dialkylamino, (linear or branched chain lower alkyl N-mono- or N,N-dialkylamino)(lower alkyl), halogen, cyano, trifluoromethyl, nitro, aryl or heteroaryl;

or a salt thereof, and a pharmaceutically acceptable carrier or diluent. Also disclosed are methods of inhibiting bacterial growth, comprising the administration of formulations comprising the compounds of formulas (I) to (V).

7 Claims, No Drawings

OTHER PUBLICATIONS

Bekhli, A.F. et al., "Synthesis of Benzo'g!quinoline Derivatives XIII. New Benzo'g!quinoline Derivatives Possessing Antimalarial Activity", Med. Parazitol. Parazit. Bolezni (19777), 46(1), 71–2, 1977, XP000910798, abstract; table 1.

Kovalenko, F.P., "Selection in vitro of Antialveococcal and Antiechinococcal Preparations", Deposited Doc. (1978), VINITI 3276–78, 15 pp. Avail.: Viniti, 1978, XP000910971, whole document.

Mikhailitsyn, F.S. et al., "Search for New Antiparasitic Agents. 8. Synthesis and Studies of Acute Toxicity, Antialveococcosis, and Antihymenolepidiasis Activity of Some 1–alkyl–4–'4–(heterylamino)phenyl!piperazines", Med. Parazitol. Parazit. Bolezni (1991), whole document.

Zhang, Jiaxun et al., "Antimalarial Effect of Dabequikne and Its Derivatives", Zhongguo Yiyao Gongye Zazhi (1989), 20(1), 15–19, 1989, XP000910806, abstract; figure 1; tables 1–4.

Bekhli, A.F. et al., "Antimalarial Drugs", Med. Parazitol. Parazit. Bolez. (1969), 38(3), 300–4, 1969, XP000910706, abstract; tables 1,2.

Petrov, O.E. et al., "In vitro Interaction of Chick Erythrocyte DNA With (substituted 4–amino) benzo'g!quinolines", Khim.–Farm. ZH. (1982), 16(11), 1304–6, 1982, XP000910712, whole document.

Kozyreva, N.P. et al., "Synthesis and Study of the Anthelmintic Activity of Some N–Heterocycles Containing 4-(4'–diethylcarbamoyl–1'–piperazinyl) Phenylamine Substituents", Khim.–Farm. Zh. (1972), 6(1), 9–12, 1972, XP000910711, see compound (X), (XI) abstract; table 1; p. 9, paragraph 3.

Belik, A.V. et al., "Prediction of Acute Toxicity of the Derivatives of Benzo'g!quinoline", Dokl. Akad. Nauk SSSR (1990), 310(5), 1144–9 'Phys. Chem.!, 1990, XP000913552, whole document.

BENZOQUINOLINE DERIVATIVES USEFUL AS ANTIBACTERIAL AGENTS

This appilcation claims benefit of Provisional No. 60/103,822 filed Oct. 9, 1998.

FIELD OF THE INVENTION

The present invention relates to pharmaceutical compositions comprising benzoquinoline derivatives and methods for using benzoquinoline derivatives as antibacterial agents. The invention also relates to novel benzoquinoline derivatives, their preparation, to pharmaceutical compositions containing them, and to methods of using them to alleviate bacterial infections.

BACKGROUND OF THE INVENTION

New classes of antibacterial agents are needed to address both the growing resistance of bacteria to present therapies and the general lack of efficacy of existing antibiotics against slow-growing organisms. Although bacterial infections were once considered well controlled, the threat posed by the emergence of multidrug-resistant organisms is now well accepted. Desirable characteristics for new antibacterial products include activity against drug resistant organisms, reduced propensity for resistance development, greater biological half-life in humans, reduced liability for allergic reactions, and broad spectrum antibacterial activity.

SUMMARY OF THE INVENTION

The present invention provides pharmaceutical compositions and formulations comprising benzoquinoline compounds having the generic formula (I):

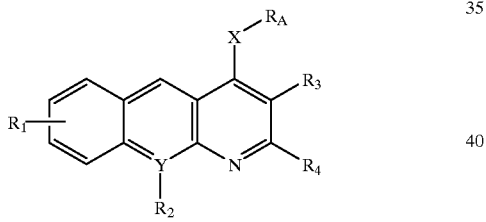

wherein:
X is selected from the group consisting of O, S, $CH_2$, $CH_2$–$CH_2$, C=O or $NR_B$;
Y is C or N;
$R_1$, $R_2$, $R_3$ and R4 are independently selected from the group consisting of hydrogen, halogen, linear or branched chain lower alky, alkenyl, alkynyl, alkoxy or acyl; and
X-$R_A$ and $R_3$, or $R_3$ and $R_4$, are optionally linked together to form a $C_3$–$C_4$ alkylene bridge wherein X is $CH_2$ or C=O
provided that:
when X is $NR_B$, then
(a) $R_B$ is hydrogen, and $R_A$ is a linear or branched chain lower alkyl, alkenyl, alkynyl, aryl, heteroaryl or cycloalkyl, cycloalkenyl, optionally interrupted by at least one heteroatom, said alkyl, alkenyl, alkynyl, aryl, heteroaryl, cycloalkyl or cycloalkenyl being optionally substituted singly or plurally by at least one of a linear or branched chain lower alkyl, alkenyl, alkynyl, acyl, alkoxy, cycloalkyl or cycloalkenyl optionally interrupted by at least one heteroatom and optionally substituted by at least one linear or branched chain lower alkyl, alkenyl, alkynyl, acyl, or alkoxy, an amino group wherein said amino group is substituted at one or two positions with a linear or branched chain lower alkyl, alkenyl, or alkynyl, (linear or branched chain lower alkyl N-mono- or N,N-dialkylamino)(lower alkyl), (linear or branched chain lower alkyl N-mono- or N,N-dialkyl)carbamyl, aryl or heteroaryl; or
(b) X, $R_A$ and $R_B$ together form a ring system comprising from about five to about twelve linked carbon atoms, said system being optionally interrupted by at least one heteroatom, optionally mono- or polyunsaturated and optionally substituted singly or plurally by at least one of a linear or branched chain lower alkyl, alkenyl, alkynyl, acyl, alkoxy, a linear or branched chain lower alkyl N-mono- or N,N-dialkylamino, (linear or branched chain lower alkyl N-mono- or N,N-dialkylamino)(lower alkyl), halogen, cyano, trifluoromethyl, nitro, aryl or heteroaryl; and
when X is O, S, $CH_2$, $CH_2$—$CH_2$ or C=O, then
(a) $R_A$ is hydrogen or a linear or branched chain lower alkyl, alkenyl, alkynyl, aryl or heteroaryl, said alkyl, alkenyl, alkynyl, aryl or heteroaryl being optionally substituted singly or plurally by at least one of a linear or branched chain lower alkyl, alkenyl, alkynyl, acyl, or alkoxy, a linear or branched chain lower alkyl N-mono- or N,N-dialkylamino, (linear or branched chain lower alkyl N-mono- or N,N-dialkylamino)(lower alkyl), halogen, cyano, trifluoromethyl, nitro, aryl or heteroaryl; and
(b) $R_3$ is a linear or branched chain lower alkyl, alkenyl, alkynyl, substituted by hydroxyphenyl, or is a linear or branched chain lower alkoxyphenyl singly or plurally substituted by $CH_2NR_CR_D$ wherein N, $R_C$ and $R_D$ together form a ring system comprising from about five to about twelve linked carbon atoms, said system being optionally interrupted by at least one heteroatom, optionally mono- or polyunsaturated and optionally substituted singly or plurally by at least one of a linear or branched chain lower alkyl, alkenyl, alkynyl, acyl, or alkoxy, a linear or branched chain lower alkyl N-mono- or NN-dialkylamino, (linear or branched chain lower alkyl N-mono- or N,N-dialkylamino)(lower alkyl), halogen, cyano, trifluoromethyl, nitro, aryl or heteroaryl;
and further provided that when Y is N, $R_2$ is absent;
or a salt thereof, and a pharmaceutically acceptable carrier or diluent.

In an additional embodiment, the invention also comprises pharmaceutical compositions and formulations comprising a compound having the generic formula (II):

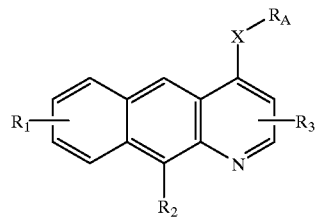

wherein:
$R_1$, $R_2$ and $R_3$ are independently selected from the group consisting of hydrogen, halogen, linear or branched chain lower alkyl, alkoxy or acyl; and X is O, S, CH$_2$, CH$_2$–CH$_2$, C=O or NR$_B$;
provided that:
   when X is NR$_B$, then
   (a) R$_B$ is hydrogen, and R$_A$ is a linear or branched chain lower alkyl, aryl, heteroaryl or cycloalkyl optionally interrupted by at least one heteroatom, said alkyl, aryl, heteroaryl or cycloalkyl being optionally substituted singly or plurally by at least one of a linear or branched chain lower alkyl, acyl, alkoxy, or cycloalkyl optionally interrupted by at least one heteroatom and optionally substituted by at least one linear or branched chain lower alkyl, acyl, or alkoxy, or a linear or branched chain lower alkyl mono- or dialkylamino, (linear or branched chain lower alkyl N-mono- or N,N-dialkylamino)(lower alkyl), (linear or branched chain lower alkyl N-mono- or N,N-dialkyl)carbamyl, aryl or heteroaryl, said aryl or heteroaryl being optionally substituted by at least one alkyl, alkenyl, or alkynyl, wherein said alkyl, alkenyl or alkynyl is optionally substituted by at least one hydroxy; or
   (b) X, R$_A$ and R$_B$ together form a ring system comprising from about five to about twelve linked carbon atoms, said system being optionally interrupted by at least one heteroatom, optionally mono- or polyunsaturated and optionally substituted singly or plurally by at least one of a linear or branched chain lower alkyl, acyl, or alkoxy, a linear or branched chain lower alkyl N-mono- or N,N-dialkylamino, (linear or branched chain lower alkyl N-mono- or N,N-dialkylamino)(lower alkyl), halogen, cyano, trifluoromethyl, nitro or aryl or heteroaryl; and
when X is O, S, CH$_2$ CH$_2$–CH$_2$ or C=O, then
   (a) R$_A$ is hydrogen or a linear or branched chain lower alkyl, alkenyl, alkynyl, aryl or heteroaryl, said alkyl, aryl or heteroaryl being optionally substituted singly or plurally by at least one of a linear or branched chain lower alkyl, alkenyl, alkynyl, acyl, or alkoxy, a linear or branched chain lower alkyl N-mono- or N, N-dialkylamino, (linear or branched chain lower alkyl N-mono- or N,N-dialkylamino)(lower alkyl), halogen, cyano, trifluoromethyl, nitro or aryl or heteroaryl; and
   (b) R$_3$ is a linear or branched chain lower alkyl substituted by hydroxyphenyl or linear or branched chain lower alkoxyphenyl singly or plurally substituted by CH$_2$NR$_C$R$_D$ wherein N, R$_C$ and R$_D$ together form a ring system comprising from about five to about twelve linked carbon atoms, said system being optionally interrupted by at least one heteroatom, optionally mono- or polyunsaturated and optionally substituted singly or plurally by at least one of a linear or branched chain lower alkyl, alkenyl, alkynyl, acyl, or alkoxy, a linear or branched chain lower alkyl N-mono- or N,N-dialkylamino, (linear or branched chain lower alkyl N-mono- or N,N-dialkylamino)(lower alkyl), halogen, cyano, trifluoromethyl, nitro, aryl or heteroaryl;
or a salt thereof, and a pharmaceutically acceptable carrier or diluent.

The present invention also provides methods for inhibiting microbial replication and preventing and/or treating microbial infections in an animal, comprising administering an antibacterial effective amount of the pharmaceutical formulations of the invention to an animal in need of such treatment. The microbial infections which may be treated by administration of the composition of the invention include drug resistant microbial inventions and multi-drug resistant microbial infections.

DETAILED DESCRIPTION OF THE INVENTION

All patents, patent applications and literature references cited herein are hereby incorporated in their entirety. In the case of inconsistencies, the present disclosure, including definitions, will control.

The present invention provides pharmaceutical compositions and formulations comprising benzoquinoline compounds having the formula (I):

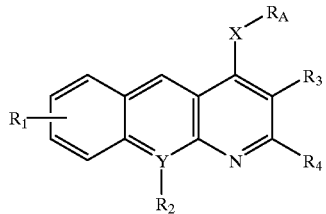

wherein:
   X is selected from the group consisting of O, S, CH$_2$, CH$_2$–CH$_2$, C=O or NR$_B$;
   Y is C or N;
   R$_1$, R$_2$, R$_3$ and R$_4$ are independently selected from the group consisting of hydrogen, halogen, linear or branched chain lower alky, alkenyl, alkynyl, alkoxy or acyl;
   X-R$_A$ and R$_3$, or R$_3$ and R$_4$, are optionally linked together to form a C$_3$–C$_4$ alkylene bridge, where X is CH$_2$ or C=O;
provided that:
   when X is NR$_B$, then
   (a) R$_B$ is hydrogen, and R$_A$ is a linear or branched chain lower alkyl, aryl, heteroaryl, cycloalkyl or cycloalkenyl optionally interrupted by at least one heteroatom, said alkyl, alkenyl, alkynyl, aryl, heteroaryl, cycloalkyl or cycloalkenyl being optionally substituted singly or plurally by at least one of a linear or branched chain lower alkyl, alkenyl, alkynyl, acyl, alkoxy, or cycloalkyl optionally interrupted by at least one heteroatom and optionally substituted by at least one linear or branched chain lower alkyl, alkenyl, alkynyl, acyl, or alkoxy, or a linear or branched chain lower alkyl mono- or dialkylamino, (linear or branched chain lower alkyl N-mono- or N,N-dialkylamino)(lower alkyl), (linear or branched chain lower alkyl N-mono- or N,N-dialyl)carbamyl, aryl or heteroaryl; or
   (b) X, R$_A$ and R$_B$ together form a ring system comprising from about five to about twelve linked carbon atoms, said system being optionally interrupted by at least one heteroatom, optionally mono- or polyunsaturated and optionally substituted singly or plurally by at least one of a linear or branched chain lower alkyl, alkenyl, alkynyl, acyl, or alkoxy, a linear or branched chain lower alkyl N-mono- or N,N-dialkylamino, (linear or branched chain lower alkyl N-mono- or N,N-dialkylamino)(lower alkyl), halogen, cyano, trifluoromethyl, nitro, aryl or heteroaryl; and
when X is O, S, CH$_2$ CH$_2$—CH$_2$ or C=O, then
   (a) R$_A$ is hydrogen or a linear or branched chain lower alkyl, alkenyl, alkynyl, aryl or heteroaryl, said alkyl, alkenyl, alkynyl, aryl or heteroaryl being optionally substituted singly or plurally by at least one of a linear or branched chain lower alkyl, alkenyl, alkynyl, acyl, or alkoxy, a linear or branched chain lower alkyl N-mono- or N,N-dialkylamino, (linear or branched chain lower alkyl N-mono- or N,N-dialkylamino)(lower alkyl), halogen, cyano, trifluoromethyl, nitro, aryl or heteroaryl; and (b) $R_3$ is a linear or branched chain lower alkyl substituted by hydroxyphenyl, or is a linear or branched chain lower alkoxyphenyl singly or plurally substituted by $CH_2NR_CR_D$ wherein N, $R_C$ and $R_D$ together form a ring system comprising from about five to about twelve linked carbon atoms, said system being optionally interrupted by at least one heteroatom, optionally mono- or polyunsaturated and optionally substituted singly or plurally by at least one of a linear or branched chain lower alkyl, acyl, or alkoxy, a linear or branched chain lower alkyl N-mono- or N,N-dialkylamino, (linear or branched chain lower alkyl N-mono- or N,N-dialkylamino)(lower alkyl), halogen, cyano, trifluoromethyl, nitro, aryl or heteroaryl;

or a salt thereof, and a pharmaceutically acceptable carrier or diluent.

In one embodiment, the invention is a pharmaceutical formulation comprising a compound of generic formula (I) as described above wherein X, $R_A$ and $R_B$ together form an N-substituted morpholine. In another embodiment, the invention is a pharmaceutical formulation comprising a compound of generic formula (I) as described above wherein X, $R_A$ and $R_B$ together form an N-substituted,N-(lower alkyl)-piperazine. In another embodiment, the invention is a pharmaceutical formulation comprising a compound of generic formula (I) as described above wherein the N-(lower alkyl) is N-ethyl. In yet another embodiment, the invention is a pharmaceutical formulation comprising a compound of generic formula (I) as described above wherein X is NH and $R_A$ is (N,N-diethyl)-dimethylene or (N,N-diethyl)-trimethylene.

The invention is also directed to a pharmaceutical composition and formulation comprising a compound of the generic formula (II):

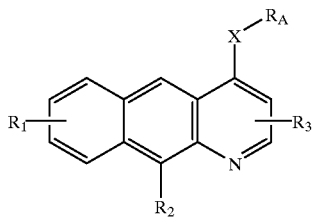

wherein:
$R_1$, $R_2$ and $R_3$ are independently selected from the group consisting of hydrogen, halogen, linear or branched chain lower alkyl, alkoxy or acyl;
X is selected from the group consisting of O, S, $CH_2$, $CH_2$–$CH_2$, C=O or $NR_B$;
provided that when X is $NR_B$, then
(a) $R_B$ is hydrogen, and $R_A$ is a linear or branched chain lower alkyl, aryl, heteroaryl or cycloalkyl optionally interrupted by at least one heteroatom, said alkyl, aryl, heteroaryl or cycloalkyl being optionally substituted singly or plurally by at least one of a linear or branched chain lower alkyl, acyl, alkoxy, or cycloalkyl optionally interrupted by at least one heteroatom and optionally substituted by at least one linear or branched chain lower alkyl, acyl, or alkoxy, or a linear or branched chain lower alkyl mono- or dialkylamino, (linear or branched chain lower alkyl N-mono- or N,N-dialkylamino)(lower alkyl), (linear or branched chain lower alkyl N-mono- or N,N-dialkyl)carbamyl, aryl or heteroaryl, said aryl or heteroaryl being optionally substituted by at least one alkyl, alkenyl, or alkynyl, wherein said alkyl, alkenyl or alkynyl is optionally substituted by at least one hydroxy; or (b) X, $R_A$ and $R_B$ together form a ring system comprising from about five to about twelve linked carbon atoms, said system being optionally interrupted by at least one heteroatom, optionally mono- or polyunsaturated and optionally substituted singly or plurally by at least one of a linear or branched chain lower alkyl, acyl, or alkoxy, a linear or branched chain lower alkyl N-mono- or N,N-dialkylamino, (linear or branched chain lower alkyl N-mono- or N,N-dialkylamino) (lower alkyl), halogen, cyano, trifluoromethyl, nitro or aryl or heteroaryl; and when X is O, S, $CH_2$, $CH_2$–$CH_2$ and C=O, then
(a) $R_A$ is hydrogen or a linear or branched chain lower alkyl, aryl or heteroaryl, said alkyl, aryl or heteroaryl being optionally substituted singly or plurally by at least one of a linear or branched chain lower alkyl, acyl, or alkoxy, a linear or branched chain lower alkyl N-mono- or N,N-dialkylamino, (linear or branched chain lower alkyl N-mono- or N,N-dialkylamino)(lower alkyl), halogen, cyano, trifluoromethyl, nitro, aryl or heteroaryl; and (b) $R_3$ is a linear or branched chain lower alkyl substituted by hydroxyphenyl, or is a linear or branched chain lower alkoxyphenyl singly or plurally substituted by $CH_2NR_CR_D$ wherein N, $R_C$ and $R_D$ together form a ring system comprising from about five to about twelve linked carbon atoms, said system being optionally interrupted by at least one heteroatom, optionally mono- or polyunsaturated and optionally substituted singly or plurally by at least one of a linear or branched chain lower alkyl, acyl, or alkoxy, a linear or branched chain lower alkyl N-mono- or N,N-dialkylamino, (linear or branched chain lower alkyl N-mono- or N,N-dialkylamino) (lower alkyl), halogen, cyano, trifluoromethyl, nitro, or aryl or heteroaryl;

or a salt thereof, and a pharmaceutically acceptable carrier or diluent.

In one embodiment, the invention comprises a pharmaceutical formulation comprising a compound of generic formula (II) as described above wherein X, $R_A$ and $R_B$ together form an N-substituted morpholine. In another embodiment, the invention comprises a compound of generic formula (II) as described above wherein X, $R_A$ and $R_B$ together form an N-substituted,N-(lower alkyl)-piperazine. In another embodiment, the invention is a pharmaceutical formulation comprising a compound of generic formula (II) as described above wherein the N-(lower alkyl) is N-ethyl. In yet another embodiment, the invention is a pharmaceutical formulation comprising the compound of generic formula (II) as described above wherein X is NH and $R_A$ is (N,N-diethyl)-dimethylene or (N,N-diethyl)-trimethylene.

The invention is also directed to pharmaceutical compositions and formulations comprising a compound having the generic formula (III):

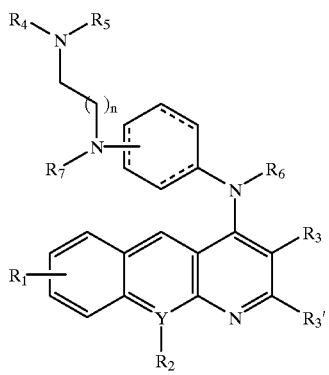

wherein:
  Y is C or N;
  $R_1$, $R_2$, $R_3$ and $R_3'$ are independently selected from the group consisting of hydrogen, halogen, linear or branched chain lower alkyl, alkoxy or acyl;
  $R_4$, $R_5$, $R_6$ and $R_7$ are independently selected from the group consisting of hydrogen, linear or branched chain lower alkyl, or acyl;
  the dashed lines indicate optional double bonds; and wherein N-$R_6$ and $R_3$, or $R_3$ and $R_3'$, are optionally linked together to form a $C_3$–$C_4$ alkylene bridge, and wherein n is an integer from about 1 to about 6;
  or a salt thereof, and a pharmaceutically acceptable carrier or diluent.

In one embodiment, the invention is a pharmaceutical formulation comprising a compound of generic formula (II) wherein $R_1$, $R_2$, $R_3$, $R_3'$, $R_6$ and $R_7$ are hydrogen; $R_4$ and $R_5$ are ethyl; and n is 2. In another embodiment, the invention is a pharmaceutical formulation comprising a compound of generic formula (III) wherein the dashed lines indicate double bonds.

The invention is also directed to a pharmaceutical compositions and formulations comprising a compound having the generic formula (IV):

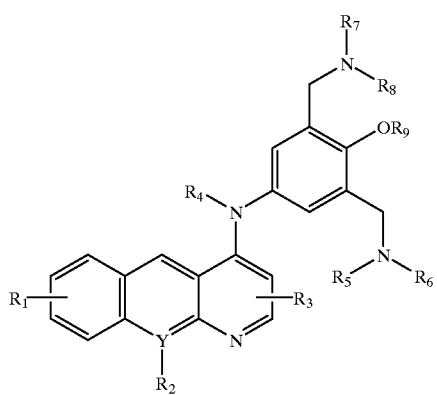

wherein:
  Y is C or N;
  $R_1$, $R_2$ and $R_3$ are independently selected from the group consisting of hydrogen, halogen, linear or branched chain lower alkyl, alkoxy or acyl;
  $R_4$, $R_5$, $R_6$, $R_7$ and $R_8$ are independently selected from the group consisting of hydrogen, linear or branched chain lower alkyl, or acyl;

$R_9$ is hydrogen, linear or branched chain lower alkyl, or acyl; and wherein when Y is N, $R_2$ is absent;

or a salt thereof, and a pharmaceutically acceptable carrier or diluent.

The invention is also directed to pharmaceutical compositions and formulations comprising a compound having the generic formula (V):

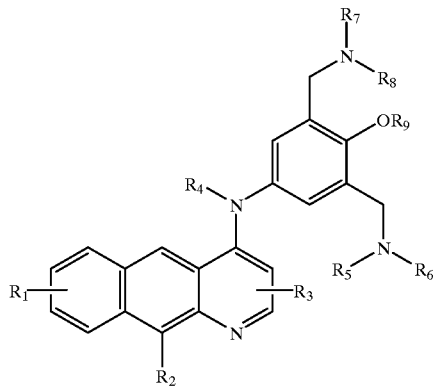

wherein:

$R_1$, $R_2$ and $R_3$ are independently selected from the group consisting of hydrogen, halogen, linear or branched chain lower alkyl, alkoxy or acyl;

$R_4$, $R_5$, $R_6$, $R_7$ and $R_8$ are independently selected from the group consisting of hydrogen, linear or branched chain lower alkyl, or acyl;

$R_9$ is selected from the group consisting of hydrogen, linear or branched chain lower alkyl, or acyl;

or a salt thereof, and a pharmaceutically acceptable carrier or diluent.

The following are particular species of the generic formulas defined above:

A. N-[4-(1-piperidinyl)phenyl]benzo[g]quinolin-4-amine

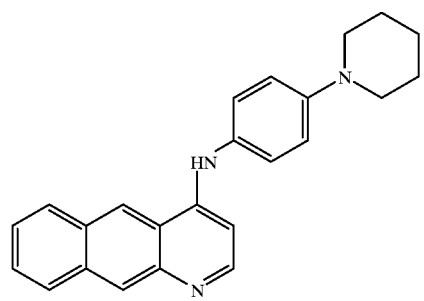

B. $N^1$-benzo[g]quinolin-4-yl-$N^4$-[2-(diethylamino)ethyl]-1,4-benzenediamine

E. N-(1-methylpentyl)benzo[g]quinolin-4-amine
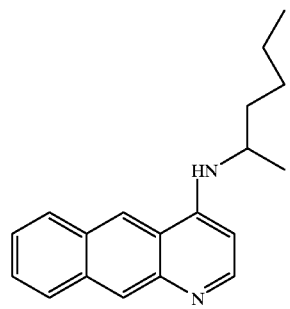
F. N-[4-(1-ethyl-4-piperidyl)phenyl]benzo[g]quinolin-4-amine
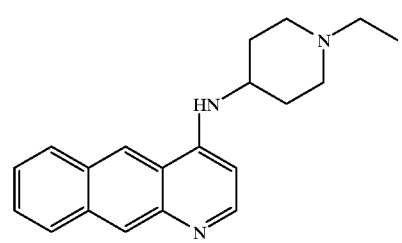
G. N-[4-(1-azepanyl)phenyl]benzo[g]quinolin-4-amine
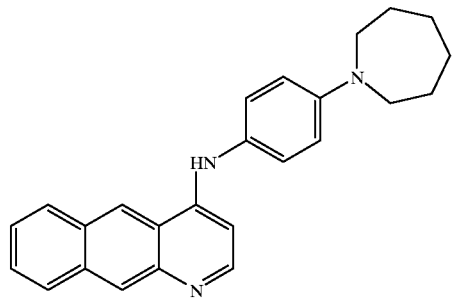
H. N-{4-[4-(3-butynyl)-1-piperazinyl]phenyl}benzo[g]quinolin-4-amine
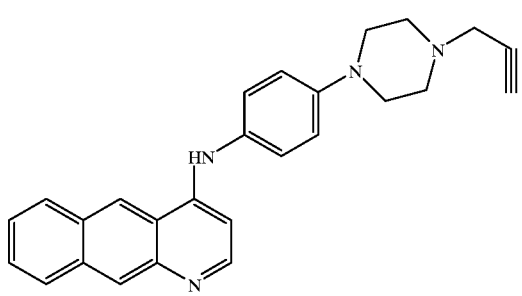
I. $N^1$-benzo[g]quinolin-4-yl-$N^4$-isopropyl-1,4,benzenediamine
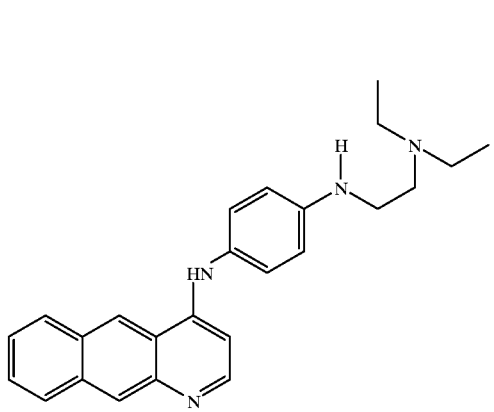
C. 3{4-[4-(benzo[g]quinolin-4-yl-amino)phenyl]-1-piperazinyl}-1-propanol
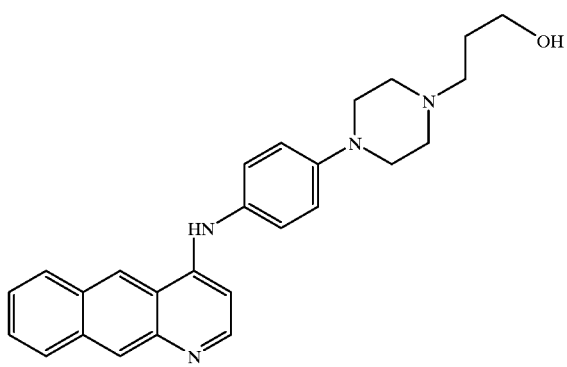
D. 4-(benzo[g]quinolin-4-yl-amino)-2,6-bis[(diethylamino)methyl]phenol
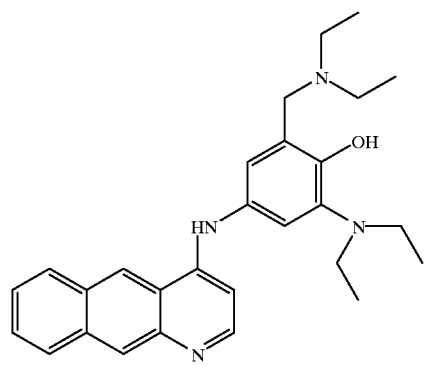

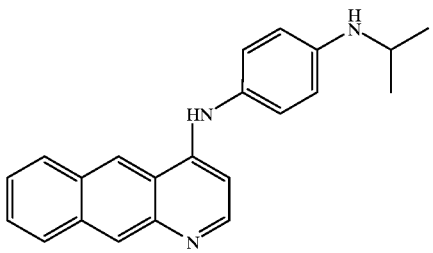

As used herein, the chemical radical names are intended to have the meaning as understood by persons of ordinary skill in the art. The following terms are specifically intended to include the definitions set forth below.

The term "heteroaryl" or "heterocylic aromatic" includes a 4–6 membered unsaturated monocyclic or fused cyclic ring containing 1 to 3 heteroatoms selected from the group consisting of N, S and O.

The term "heteroatom" includes nitrogen, oxygen and sulfur, as well as any atom other than carbon.

The term "lower alkyl" includes an alkyl group having from 1 to 4 carbon atoms.

The term "carbonyl" or "amino carbonyl" refers to the group $H_2NC(O)$.

The pharmaceutical formulations of the present invention comprise the compounds disclosed herein, which exhibit antibacterial activity. Without wishing to be bound by theory, it is believed that the antimicrobial activity of the compounds is due at least in part to their ability to inhibit microbial RNA polymerase enzymatic activity. Useful compounds may be identified by their ability to bind to and/or inhibit the enzymatic activity of, RNA polymerase from any microbial source, preferably bacterial. Compounds that exhibit RNA polymerase inhibitory activity in vitro can then be tested for in vivo antimicrobial activity. Alternatively, the antimicrobial activity of a compound may be tested directly.

A general procedure for the preparation of N-substituted benzo[g]quinolin-4-amines of structure (4) is described herein.

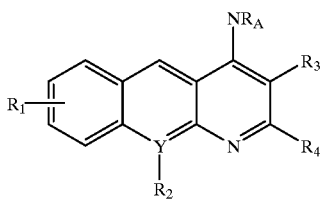

4

Substituted 2,3-dihydrobenzo[g]quinolin 4 (1H)-ones (1) (Bekhli and Kozyreva Khim. Geteotsikl. Soedin 1996, 296)

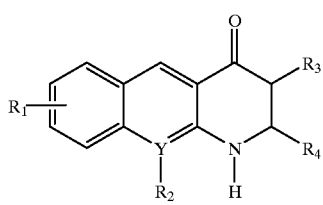

1 are first oxidized to the corresponding benzo[g]quinolin-4-ols (2).

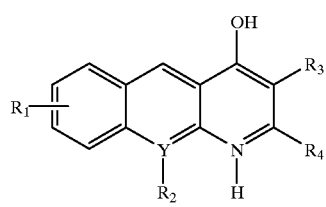

2

It is preferred that the oxidant be chosen from a group consisting of 2,3 dichloro-5,6 dicyanobenzoquinone (DDQ) or manganese (IV) oxide. The resultant phenols are then converted into their corresponding 4-halobenzo[g]quinolines (3a,3b)

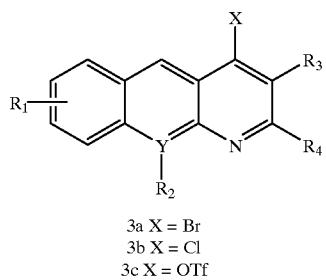

3a X = Br
3b X = Cl
3c X = OTf utilizing reagents chosen from a group consisting of phosphorous pentabromide, phosphorous tribromide, and phosphorous oxychloride in the presence of a base chosen from a group consisting of tertiary amine bases, preferably N,N-dimethyl aniline and alkali bases preferably potassium carbonate. Alternatively, substituted 4-triflouromethanesulfonylbenzo[g]quinolines (3c) can be synthesized from their corresponding phenols utilizing triflouromethane sulfonic anhydride in the presence of a tertiary amine base, preferably pyridine.

Substituted 4-halobenzo[g]quinolines (3a,3b) (Wagaw and Buchwald J. Org. Chem. 1996, 7240. Wolfe, Wagaw and Buchwald J Am. Chem. Soc. 1996, 7215. Louie, Hartwig Tetrahedron Lett. 1995, 3609. Driver, Hartwig J. Am. Chem. Soc. 1996, 7217. Wolfe, Rennels, and Buchwaid Tetrahedron 1996, 7525. Wolfe and Buchwald J.Am. Chem. Soc. 1997, 6054.) and substituted 4-triflouromethane sulfonyl benzo[g]quinolines (3c) (Louie, Driver, Haman, and Hartwig J. Am. Chem. Soc. 1997, 1268; Wolfe and Buchwald J. Org. Chem. 1997, 1264) may be agitated at the 4-position with a group consisting of primary and secondary amines in the presence of a metal complex catalyst, where the metal species is chosen from a group consisting of nickel, palladium, and platinum, to afford the desired N-substituted benzo[g]quinolin-4-amines (4).

DETAILED DESCRIPTION OF THE EXEMPLARY EMBODIMENTS

The following is a chemical process for the efficient production of – substituted benzo[g]quinolin-4-amines (4) which are useful as antibacterial agents.

A. Production of Benzo[g]quinolin-4-ols (2) From the Oxidation of 2.3 Dihydrobenzo[g]quinolin-4-(1H)-ones (1).

2,3 dihydrobenzo[g]quinolin-4-(1H)-one (5)

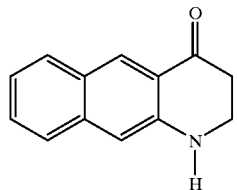

is dissolved in an aromatic solvent, preferably toluene, under a nitrogen atmosphere. To this solution is added DDQ (at least 1 equivalent but preferably 1.3 equivalents). The reaction mixture is then heated to reflux for a period of approximately 1–3 hr, after which time the mixture is cooled to room temperature and concentrated to a residue in vacuo. The residue is then applied directly to a silica gel column using methanol/methylene chloride preferably in a 1:9 ratio as eluent, to afford crude benzo[g]quinolin-4-ol which was used without further purification. Alternatively, the oxidation may be carried out in the following manner: 2,3-dihydrobenzo[g]quinolin-4-(1H)-one (1) is dissolved in an ethereal solvent, preferably tetrahydrofuran, under a nitrogen atmosphere. To this solution is then added manganese (IV) oxide (between 1 and 10 equivalents but preferably 8 equivalents). The reaction mixture is then heated for a period of approximately 1–3 hr, after which time the reaction mixture is filtered through diatomaceous earth and the filter cake washed with methanol/methylene chloride preferably in a 5:95 ratio. The filtrates were then reduced in vacuo to afford crude benzo[g]-quinolin-4-ol (6)

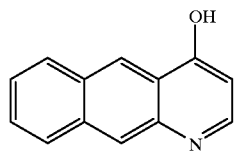

which was used without further purification.

B. Production of 4-Bromo (7a), Chloro (7b), Triflouromethanesulfonic (7c)-Benzo[g]Quinolines from Benzo[g]Quinolin-4-ol (6).

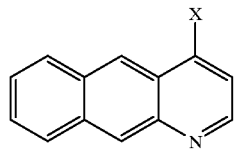

7a X = Br
7b X = Cl
7c X = OTf

4-Bromination and 4-chlorination of benzo[g]quinolin-4-ol (6) may be accomplished in the following manner. Crude benzo[g]quinolin-4-ol (6) was dissolved in acetonitrile and cooled to a temperature of approximately 0° C. under a nitrogen atmosphere. A tertiary amine base, preferably N,N-dimethylaniline (between 1–5 equivalents but preferably 5 equivalents) is then added to the solution. Alternatively an alkali base, preferably potassium carbonate (between 1–5 equivalents but preferably 5 equivalents) may be employed. In either case, the halogenation agent is chosen from a group consisting of phosphorous oxychloride, phosphorous tribromide, phosphorous pentabromide (between 1–2 equivalents but preferably 1.5 equivalents) is added to the cooled solution. The solution is then heated to reflux for a period of 2–6 hr, the mixtures then cooled to room temperature, slowly poured onto an ice water slurry and extracted with methylene chloride three times. The organic layers are combined, washed with brine, dried over magnesium sulfate and concentrated in vacuo to a residue. The residue is then applied to a silica gel column and eluted with hexane/ethyl acetate (9:1 then 8:2 then 7:3) to afford 4-halobenzo[g] quinoline (7a, 7b).

Alternatively, 4-triflouromethanesulfonic benzo[g] quinolines (7c) may be synthesized and used in an equivalent fashion to the 4-halobenzo[g]quinoline derivatives in the ultimate step in the synthesis. Benzo[g]quinolin4-ol (6) is dissolved in methylene chloride under a nitrogen atmosphere and cooled to a temperature of less than 0° C. To this is added a tertiary amine base, preferably triethyl amine (between 1 and 2 equivalents but preferably 1.5 equivalents) followed by the addition of triflouromethanesulfonic anhydride (between 1 and 2 equivalents but preferably 1.2 equivalents). The mixture is then stirred and allowed to warm to room temperature and allowed to stir for 1–4 hr. The reaction mixture is then quenched with water and the organic phase removed and the aqueous phase washed with two portions of methylene chloride. The combined organic layers are washed with water, saturated sodium bicarbonate, water, and finally brine. The organic phase is then dried over magnesium sulfate and concentrated in vacuo and used crude immediately in the next step.

C. Coupling of 4-Halo (7a,7b) and 4-Triflourosulfonic (7c) Benzo[g]Quinoline Derivatives and Primary and Secondary Amines Utilizing Metal Complex Catalyst.

From a group consisting of substituted 4-bromo (7a), 4-chloro (7b), and 4-triflouromethanesulfonic (7c) benzo[g] quinoline and a selected primary, secondary amine (at least 1.0 equivalents but preferably 1.2 equivalents) is dissolved in an aromatic solvent, preferably toluene. To this is added a metal complex catalyst with the metal chosen from a group consisting of nickel, palladium, and platinum in this instance tris (dibenzylideneacetone) dipalladium (Pd$_2$(dbba)$_3$) (at least a catalytic amount 0.02 equivalent) and bis (diphenylphosphino)-ferrocene (DPPF) (at least a catalytic amount 0.04 equivalent) and an alkali alkoxide preferably sodium t-butoxide (at least 1.0 equivalent but preferably 1.4 equivalent). The mixture is then refluxed under a nitrogen atmosphere for a period of 1–3 hr. After which time the mixture is cooled to room temperature and concentrated in vacuo to a residue and applied to a silica gel column using hexane/EtOAc/TEA as eluent (50:50:2 then 60:40:2) to afford N-substituted benzo[g]quinolin 4-amines (4).

The following syntheses are for exemplary compounds of the invention:

EXAMPLE 1

For the preparation of N-[4-(1-piperidinyl)phenyl]benzo[g] quinolin-4-amine (8) from the aryl bromide 7a.

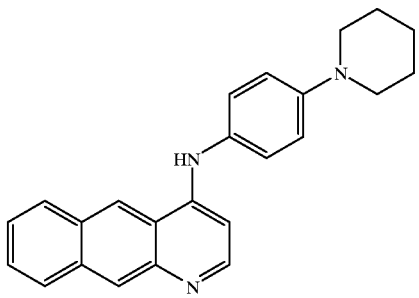

Step 1. To 1 g of 2,3-Dihydrobenzo[g]quinolin-4(1H)-one (5) (5.07 mmol) in 20 mL of toluene (0.25 M) under a nitrogen atmosphere was added 1.5 g of 2,3-dichloro-5,6-dicyanobenzoquinone (DDQ, 1.3 equivalents). The reaction mixture was heated to reflux and monitored by TLC until completion (approximately 2 h). After cooling to rt, the mixture was concentrated in vacuo then filtered through a silica plug using 10% methanol in methylene chloride to afford crude phenol (6). Subsequently, the crude phenol was directly subjected to the halogenation conditions of step 2.

Step 2. Crude benzo[g]quinolin-4-ol (6) (5.07 mmol) was dissolved in 50 mL of acetonitrile (0.1 M) and cooled to 0° C. under a nitrogen atmosphere. N,N-dimethylaniline (3.2 mL, 5 equivalents) was added followed by 3.3 g of phosphorus pentabromide (1.5 equivalents). After removal of the bath, the mixture was heated to reflux and followed by TLC until complete. Upon cooling to rt, the mixture was slowly poured onto ice water and extracted with methylene chloride three times. The organic layers were combined, washed with brine, dried with magnesium sulfate, and concentrated in vacuo. Flash chromatography (gradient: 9:1 to 8:2 to 7:3 hexanes:EtOAc) afforded 736 mg of clean 4-bromobenzo [g]quinoline (7a) in 55% yield for the 2 steps.

Step 3. 4-Bromobenzo[g]quinoline (7a) (140 mg, 0.54 mmol), 4-(I-piperidino)aniline (115 mg, 1.2 equivalents), tris(dibenzylideneacetone)dipalladium (Pd$_2$(dbba)$_3$, (10 mg, 0.02 equivalents), 1,1'-bis(diphenylphosphino)ferrocene (DPPF, 12 mg, 0.04 equivalents) and sodium t-butoxide (73 mg, 1.4 equiv) in 5 mL of dry toluene were refluxed under a nitrogen atmosphere until observed complete by TLC (approximately 1 h). The mixture was concentrated in vacuo and purification by flash chromatography (gradient: 5 50:50:2 to 60:40:2 hexane:EtOAc:Et$_3$N) provided 148 mg of clean N-[4-(1-piperidinyl)phenyl]benzo[g]quinolin-4-amine (8) (77% yield).

EXAMPLE 2

For the preparation of N-[4-(1-piperidinyl)phenyl]benzo[g] quinolin-4-amine (8) from aryl chloride (7b).

Step 1. To 500 mg of 2,3-Dihydrobenzo[g]quinolin-4 (IH)-one (1, 2.53 mmol) in 25 mL of dry tetrahydrofuran (0.25 M) under a nitrogen atmosphere was added 1.76 g manganese(IV) oxide (8 equivalents). The reaction mixture was heated to reflux and monitored by TLC until completion. The crude reaction mixture was filtered through a celite plug using 5% methanol in methylene chloride to afford 445 mg of relatively clean benzo[g]quinolin-4-ol (6) in 90% yield. Subsequently, the phenol was directly subjected to the halogenation conditions without further purification.

Step 2. Under a nitrogen atmosphere, benzo[g]quinolin-4-ol (6) (100 mg, 0.51 mmol) was refluxed in 2 ml of phosphorus oxychloride (0.25 M) in the presence of N,N-dimethylaniline (0.25 mL, 3.8 equivalents) until deemed complete by TLC. Removal of the excess phosphorus oxycloride in vacuo and flash chromatography (gradient: 9:1 to 8:2 to 7:3 hexanes:EtOAc) afforded 108 mg of clean 4-chlorobenzo[g]quinoline (7b) in quantitative yield.

Step 3. 4-Chlorobenzo[g]quinoline (7b) (50 mg, 0.23 mmol), 4-(1-piperidino) aniline (50 mg, 1.2 equivalents), bis(1,5-cyclooctadiene)nickel(O) (Ni(COD)$_2$ 1.5 mg, 0.02 equivalents), 1,1'-bis(diphenylphosphino)ferrocene (DPPF, 5 mg, 0.04 equivalents) and sodium t-butoxide (31 mg, 1.4 equiv) in 2.5 mL of dry toluene were refluxed under a 5 nitrogen atmosphere until observed complete by TLC. The mixture was concentrated in vacuo and purified by flash chromatography (gradient: 50:50:2 to 60:40:2 hexane: EtOAc:Et$_3$N) to provide 69 mg of clean N-[4-(1-piperidinyl) phenyl]benzo[g]quinolin-4-amine (8), 85% yield.

EXAMPLE 3

The preparation of N-[4-(1-piperidinyl)phenyl]benzo[g] quinolin-4-amine (8) from aryl triflate (7c).

Step 1. To benzo[g]quinolin-4-ol (6), 42 mg, (0.22 mmol) in 2 mL of methylene chloride (0.1 M) under a nitrogen atmosphere at 0° C. was added triethylamine (45 μL, 0.32 mmol) followed by triflic anhydride (47 gL, 0.28 mmol) dropwise. The mixture was stirred while allowing to warm to rt and continued until complete by TLC (about 1.5 hr). The reaction mixture was quenched with water and extracted twice with methylene chloride. The combined organic layers were washed with water, saturated sodium bicarbonate, water, then brine. After drying with magnesium sulfate, the crude triflate (7c) was concentrated in vacuo and immediately used in the coupling step.

Step 2. 4-triflic benzo[g]quinoline (7c), (0.22 mmol), 4-(1-piperidino)aniline (57 mg, 0.32 mmol), tris (dibenzylideneacetone)dipalladium (Pd$_2$(dbba)$_3$, 5 mg, 0.05 equivalent), 1,1'-bis(diphenylphosphino)ferrocene (DPPF, 12 mg, 0.1 equivalent) and sodium t-butoxide (31 mg, 0.32 mmol) in 3.6 mL of dry toluene were refluxed under a nitrogen atmosphere until observed complete by TLC (approximately 1.5 hr). The mixture was concentrated in vacuo and purification by flash chromatography (gradient: 5% methanol to 10% methanol:EtOAc) provided 52 mg mixture (approximately 1:1 ratio) of N-[4-(1-piperidinyl) phenyl]benzo[g]quinolin-4-amine (8), 77% yield) and benzo [g]quinolin-4-ol (6).

Identification of RNA polymerase inhibitors

The compounds useful for inclusion in the pharmaceutical formulations of the invention can be identified by their ability to bind to, and/or inhibit the activity of, one or more bacterial RNA polymerases. RNA polymerase as used herein refers to DNA-dependent RNA polymerase holoenzyme, which is a complex consisting of five protein subunits: two copies of the a subunit and one copy each of the β, β', and σ subunits. The α, β and β' subunits are invariant in a given bacterial species and together form core RNA polymerase.

a. Binding assays

The ability of a candidate antimicrobial compound to bind to RNA polymerase can be measured using any method known in the art. Typically, purified RNA polymerase holoenzyme, or individual subunits thereof, are contacted with a plurality of compounds, and binding is monitored. Useful methods for measuring binding include without limitation those disclosed in U.S. Pat. Nos. 5,585,277 and 5,679,582.

b. Functional assays

RNA polymerase inhibition activity of a compound can be detected by including the compound in an in vitro transcription reaction and comparing the level of transcription that occurs in the presence and absence of the compound. A typical transcription reaction (50 $\mu$l) contains transcription buffer (50 mM Tris-HCI, pH 8.0, 200 mM KCl, 10 mM MgCl2, 10 mM DTT and 1.5 $\mu$M BSA); 1 $\mu$g of DNA template; 4 $\mu$M UTP containing 5 $\mu$Ci of [$\alpha$-$^{32}$P] UTP; 400 $\mu$M each of ATP, GTP, and CTP; and RNA polymerase. After incubation for 60 minutes at 25° C., the reaction is terminated with 100 $\mu$l 10% TCA, which also precipitates the newly transcribed RNA, and incorporation of radioactivity into RNA is quantified. The $IC_{50}$ (expressed in $\mu$g/ml) is the concentration of a compound that inhibits RNA polymerase activity by 50%. Candidate antimicrobial compounds are identified as those that cause a detectable inhibition of RNA polymerase activity (i.e., exhibit an $IC_{50}$ of less than about 16 $\mu$g/ml).

Measurement of Antimicrobial Activity

The antimicrobial activity of a compound or formulation according to the invention is determined by exposing a culture comprising a bacterial species to different concentrations of the compound or formulation and monitoring the effects on growth relative to a control culture not exposed to the compound. Any method known in the art may be used to assess bacterial growth. Antimicrobial effects are expressed as Minimal Inhibitory Concentration (MIC) and Minimum Bactericidal Concentration (MBC).

a. MIC

The minimal inhibitory concentration (MIC) is defined as the lowest concentration of antimicrobial agent that completely inhibits growth of the organism in the microliter plate. The MIC is expressed as a range between the concentration at which no growth is observed and the concentration of the dilution which immediately follows.

Typically, MIC is measured using a broth microdilution assay as follows. Dilution of candidate antimicrobial compounds in culture medium is performed in a sterile, covered 96-well microtiter plate with flat bottom wells (Costar #9017). The final concentrations of the compounds are typically 100, 50, 25, 12.5, 6.25, 3.12, 1.56, 0.78, 0.39, 0.20, 0.10, and 0.05 $\mu$g/mL, respectively. Culture medium only (containing no bacteria) is also included as a negative control for each plate. Ampicillin and rifamnpin are used as positive controls against all bacterial strains in every experiment.

The overnight culture of a single colony is diluted in sterile medium so that, after inoculation, each well contains approximately $5 \times 10^5$ CFU/mL. Within 15 minutes of preparation, 50 mL of the adjusted inoculum suspension is added to the microliter plate. Each well is diluted with an equal volume of the antimicrobial compounds or control solution. The inoculated microtiter plate is typically incubated at 35° C. for 16–20 hours. The turbidity of each well is determined by measuring the absorbance at 595 nm using a BioRad Model 3550-UV microplate reader.

Antimicrobial compounds are those that exhibit an MIC of less than 16 $\mu$g/mL.

b. MBC

The minimum bactericidal concentration (MBC) is defined as the concentration of antimicrobial agent from which no colonies grow on petri plates or in the medium. In practice, the MBC is arbitrarily defmed as the concentration at which a 1000-fold reduction in colony forming units is observed with respect to the original inoculum (survival of 0.1%). Typically, the wells from a MIC microliter plate using a 96-well inoculation grid into a fresh microliter plate containing 100 $\mu$L Mueller-Hinton broth per well. The MBC plates are incubated at 37° C. for 16–20 hrs and the MBC values are determined.

Antimicrobial compounds are those that exhibit an MBC of less than 16 $\mu$g/mL

Specificity determinations

It will be understood that useful antimicrobial compositions and formulations act selectively on microbial pathogens. In vitro and/or in vivo criteria may be used to determine specificity. That is, the inhibitory activity of a particular compound towards an animal RNA polymerase may be measured in parallel with a bacterial RNA polymerase. Preferably, antimicrobial compounds exhibit an $IC_{50}$ for mammalian, e.g., human, RNA Polymerase II that is at least ten-fold higher (i.e., less effective) than that for a bacterial RNA polymerase.

Furthermore, the effect of the compositions on animal cells is measured. Cytotoxicity ($TD_{50}$) is expressed as the concentration at which 50% of the cells are dead. Preferably, antimicrobial compounds according to the invention exhibit a $TD_{50}$ of less than about 5.

Methods for Preventing and Treating Microbial Infections

The present invention provides methods for inhibiting the replication of microorganisms, which comprise contacting a microorganism with an amount of an benzoquinoline derivative sufficient to inhibit its growth. The invention also provides methods for preventing or treating microbial infection in an animal, which comprise administering to an animal in need of antimicrobial treatment an antimicrobial-effective amount of a composition or formulation comprising a benzoquinoline derivative disclosed herein.

As used herein, the term "treatment" with regard to a microbial infection includes preventing, retarding, and/or reducing a disease, pathological condition or one or more symptoms thereof, in animals, particularly mammals, and most particularly humans. An antimicrobial effective amount is an amount that results in any improvement in one or more clinical or histological symptoms or diagnostic markers observed by a medical practitioner or determined by quantitative or semiquantitative techniques. Non-limiting examples of appropriate techniques include without limitation analysis of blood and urine. Any suitable assay may be used for determining antimicrobial effective amounts without undue experimentation, taking into account the route of administration and the age, sex, weight, species and condition of the particular patient.

Usually, a daily dosage of active ingredient can be from about 0.5 to about 100 mg per kg of body weight, preferably from about 5 to about 50 mg per kg per day and most preferably from about 10 to about 25 mg per kg per day. The total dosage may be administered in multiple doses or in a sustained release form. The dosages may be increased when treating severe or life-threatening infections.

In practicing the methods of the invention, benzoquinoline derivatives can be administered by any means that produces contact of the active agent with bacteria in the body of an animal, including. They can be administered by any conventional means, including without limitation oral, mucosal, intranasal, parenteral, topical, subcutaneous, intradermal, intramuscular, and intravenous routes.

The compounds and formulations of the present invention may be used for prevention and treatment of a wide variety of bacterial infections, including without limitation diseases of the skin, e.g., endocarditis, acne and skin ulcers; gastroenteritis; colitis; meningitis; keratinitis; conjunctivitis; diseases of the urinary and genital tracts, e.g., syphilis and gonorrhea; breast disease (mastitis); osteomyelitis; otitis; as well as diseases of the lungs, e.g. pneumonia and tuberculosis. The compounds are generally active in treating diseases caused by Staphylococcus aureus. In addition, the compounds are valuable for sterilizing the gut in the course of surgery.

Pharmaceutical Formulations

The present invention provides pharmaceutical formulations comprising the benzoquinoline derivatives disclosed herein in conjunction with a pharmaceutically acceptable carrier or diluent.

The formulations of the present invention can be solutions, suspensions, emulsions, syrups, elixirs, capsules, tablets, and the like. The compositions may contain a suitable carrier, diluent, or excipient, such as sterile water, physiological saline, glucose, or the like. Moreover, the formulations can also be lyophilized, and/or may contain auxiliary substances, such as wetting or emulsifying agents, pH buffering agents, adjuvants, gelling or viscosity enhancing additives, preservatives, flavoring agents, colors, and the like, depending upon the route of administration and the preparation desired Standard texts, such as "Remington's Pharmaceutical Science", 17th Ed., 1985, incorporated herein by reference, may be consulted to prepare suitable preparations, without undue experimentation.

The formulations can include powdered carriers, such as lactose, sucrose, mannitol, starch, cellulose derivatives, magnesium stearate, stearic acid, and the like. Further, tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. The formulations can also contain coloring and flavoring to enhance patient acceptance.

In general, water, a suitable oil, saline, aqueous dextrose (glucose), and related sugar solutions and glycols such as propylene glycol or polyethylene glycols such as propylene glycol or polyethylene glycols are suitable carriers for parenteral solutions. Solutions for parenteral administration contain preferably a water soluble salt of the active ingredient, suitable stabilizing agents, and, if necessary, buffer substances.

Antioxidants such as, for example, sodium bisulfate, sodium sulfite, citric acid and its salts, sodium EDTA, ascorbic acid, and the like can be used either alone or in combination with other suitable antioxidants or stabilizing agents typically employed in the pharmaceutical compositions. In addition, parenteral solutions can contain preservatives, such as, for example, benzalkonium chloride, methyl- or propyl-paraben, chlorobutanol and the like.

The formulations can also include any of disintegrants, lubricants, plasticizers, colorants, and dosing vehicles. Suitable pharmaceutical carriers are described in Remington's Pharmaceutical Sciences, A. Osol, a standard reference text in this field.

In order for a composition to be administered to an animal or human, and for any particular method of administration, it is preferred to determine the toxicity, such as by determining the MIC and MBC (see above) in a suitable animal model, e.g., a mouse; the dosage of the composition(s), and the concentration of components in the composition; and the timing of administration in order to maximize the antimicrobial response. Such factors can be determined without undue experimentation by such methods as titrations and analysis of sera for antibodies or antigens, e.g., by ELISA and/or EFFIT analysis. Such determinations do not require undue experimentation from the knowledge of the skilled artisan, the present disclosure and the documents cited herein.

Suitable formulations typically contain from about 1 to about 1000 mg of active ingredient per dosage unit. In these pharmaceutical compositions, the active ingredient will ordinarily be present in an amount of about 0.5 to about 95%, by weight, based on the total weight of the composition.

EXAMPLE 4

Biological Activity of Benzoquinolines

The following experiments were performed to evaluate the biological activity of the benzoquinoline compounds disclosed herein.

a. In vitro:

The compounds of the invention were included at a range of concentrations in in vitro transcription reactions containing purified RNA polymerase derived from either S. aureus, E. coli, or human, and template DNA comprising a pTaq promoter. The reaction conditions and analytical method are described above.

The concentration of each compound that inhibited RNA polymerase activity by 50%, i.e., the $IC_{50}$, is shown in Table 1.

The results indicated that each of the compounds selectively inhibited bacterial RNA polymerase relative to human RNA polymerase; in all cases, S. aureus RNA polymerase was the most sensitive to the inhibitory effects of the compounds. Compound N-[4-(1-piperidinyl)phenyl]benzo[g]quinolin-4-amine exhibited the highest degree of selectivity for bacterial RNA polymerases.

b. In vivo:

The antimicrobial activities of the compounds of the invention, expressed as MIC and MBC, were determined as described above, using as tester strains wild-type S. aureus, rifampicin-resistant S. aureus, wild-type E. coli, and E. coli cells that had been permeabilized.

Compound N-[4-(1-piperidinyl)phenyl]benzo[g]quinolin-4-amine exhibited the most potent antimicrobial activity against s. aureus but was less effective against E. coli.

TABLE 1

|  | MIC ($\mu$g/mL) | | | | MBG ($\mu$g/mL) | | | |
| --- | --- | --- | --- | --- | --- | --- | --- | --- |
|  | E. coli (MCR106) | E. coli (BAS) | S. Aureus | S. Aureus (Rif-res) | E. coli (MCR106) | E. coli (BAS) | S. Aureus | S. Aureus (Rif-res) |
| N-[4-(1-piperidinyl)phenyl]benzo[g]quinolin-4-amine | >64 | 2 | 2 | 2 | >64 | 2 | 4 | 2 |
| $N^1$-benzo[g]quinolin-4-yl-$N^4$-[2-(diethylamino)ethyl]-1,4 | 8 | 4 | 16 | 8 | 16 | 16 | 16 | 8 |

TABLE 1-continued

|  | MIC (μg/mL) | | | | MBG (μg/mL) | | | |
| --- | --- | --- | --- | --- | --- | --- | --- | --- |
|  | E. coli (MCR106) | E. coli (BAS) | S. Aureus | S. Aureus (Rif-res) | E. coli (MCR106) | E. coli (BAS) | S. Aureus | S. Aureus (Rif-res) |
| benzenediamine |  |  |  |  |  |  |  |  |
| 3{4-[4-(benzo[g]quinolin-4-yl-amino)phenyl]-1-piperazinyl}-1-propanol | 16 | 8 | 32 | 8 | 64 | 8 | 32 | 8 |
| N-{5-benzo[g]quinolin-4-yl-3-[(diethylamino)methyl]-2-methylbenzyl}-N-ethyl-1-ethanamine | 64 | 16 | 64 | 32 | >64 | 16 | 64 | 64 |
| N-(1-methylpentyl)benzo[g]quinolin-4-amine | >64 | 8 | 16 | 8 | >64 | 16 | 16 | 16 |
| N-[4-(1-ethyl-4-piperidyl)phenyl]benzo[g]quinolin-4-amine | 32 | 32 | 64 | 32 | 32 | 32 | 64 | 32 |
| N-[4-(1-azepanyl)phenyl]benzo[g]quinolin-4-amine | >64 | >64 | 2 | 1 | >64 | >64 | 2 | 1 |
| N-{4-[4-(3-butynyl)-1-piperazinyl]phenyl}benzo[g]quinolin-4-amine | >64 | >64 | 16 | 16 | >64 | >64 | 16 | 16 |
| $N^1$-benzo[g]quinolin-4-yl-$N^4$-isopropyl-1,4,benzenediamine | >64 | >64 | 8 | 32 | >64 | >64 | 8 | 32 |

What is claimed is:

1. A pharmaceutical composition comprising a compound of formula (II):

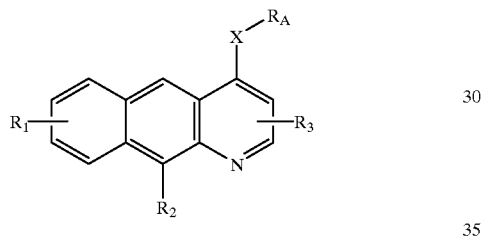

wherein:

$R_1$, $R_2$ and $R_3$ are independently selected from the group consisting of hydrogen, halogen, linear or branched chain lower alkyl, alkoxy or acyl;

X is selected from the group consisting of O, S, $CH_2$, $CH_2$–$CH_2$, C=O or $NR_B$; provided that when X is $NR_B$, then (a) $R_B$ is hydrogen, and $R_A$ is a linear or branched chain lower alkyl, aryl, heteroaryl or cycloalkyl optionally interrupted by at least one heteroatom, said alkyl, aryl, heteroaryl or cycloalkyl being optionally substituted singly or plurally by at least one of a linear or branched chain lower alkyl, acyl, alkoxy, or cycloalkyl optionally interrupted by at least one heteroatom and optionally substituted by at least one linear or branched chain lower alkyl, acyl, or alkoxy, or a linear or branched chain lower alkyl mono- or dialkylamino wherein said linear or branched chain lower alkyl mono- or dialkylamino is not ethyl or diethylamino, (linear or branched chain lower alkyl N-mono- or N,N-dialkylamino) (lower alkyl), (linear or branched chain lower alkyl N-mono- or N,N-dialkyl)carbamyl, aryl or heteroaryl, said aryl or heteroaryl being optionally substituted by at least one alkyl, alkenyl, or alkynyl, wherein said alkyl, alkenyl or alkynyl is optionally substituted by at least one hydroxy;

or (b) X, $R_A$ and $R_B$ together form a ring system comprising from about five to about twelve linked carbon atoms, said system being optionally interrupted by at least one heteroatom, optionally mono- or polyunsaturated and optionally substituted singly or plurally by at least one of a linear or branched chain lower alkyl, acyl, or alkoxy, a linear or branched chain lower alkyl N-mono- or N,N-dialkylamino, (linear or branched chain lower alkyl N-mono- or N,N-dialkylamino)(lower alkyl), halogen, cyano, trifluoromethyl, nitro or aryl or heteroaryl; and when X is O, S, $CH_2$, $CH_2$–$CH_2$ or C=O, then (a) $R_A$ is hydrogen or a linear or branched chain lower alkyl, aryl or heteroaryl, said alkyl, aryl or heteroaryl being optionally substituted singly or plurally by at least one of a linear or branched chain lower alkyl, acyl, or alkoxy, a linear or branched chain lower alkyl N-mono- or N,N-dialkylamino, (linear or branched chain lower alkyl N-mono- or N,N-dialkylamino) (lower alkyl), halogen, cyano, trifluoromethyl, nitro or aryl or heteroaryl; and (b) $R_3$ is a linear or branched chain lower alkyl substituted by hydroxyphenyl, or is a linear or branched chain lower alkoxyphenyl singly or plurally substituted by $CH_2NR_CR_D$ wherein N, $R_C$ and $R_D$ together form a ring system comprising from about five to about twelve linked carbon atoms, said system being optionally interrupted by at least one heteroatom, optionally mono- or polyunsaturated and optionally substituted singly or plurally by at least one of a linear or branched chain lower alkyl, acyl, or alkoxy, a linear or branched chain lower alkyl N-mono- or N,N-dialkylamino, (linear or branched chain lower alkyl N-mono- or N,N-dialkylamino)(lower alkyl), halogen, cyano, trifluoromethyl, nitro, or aryl or heteroaryl;

or a salt thereof, and a pharmaceutically acceptable carrier or diluent.

2. The pharmaceutical composition of claim 1 wherein X, $R_A$ and $R_B$ together form an N-substituted morpholine.

3. The pharmaceutical composition of claim 1 wherein X, $R_A$ and $R_B$ together form an N-substituted,N-(lower alkyl)-piperazine.

4. The pharmaceutical composition of claim 3 wherein the N-(lower alkyl) is N-ethyl.

5. The pharmaceutical composition of claim 1 wherein X is NH and $R_A$ is (N,N-diethyl)-dimethylene or (N,N-diethyl)-trimethylene.

6. A method for inhibiting microbial replication comprising contacting a microorganism with an effective amount of a pharmaceutical composition of claim 1 to inhibit its growth.

7. A method for preventing and/or treating microbial infections in an animal, comprising administering to an animal in need of antimicrobial treatment an antimicrobial effective amount of a pharmaceutical composition of claim 1.

* * * * *